(12) United States Patent
Park et al.

(10) Patent No.: US 10,646,447 B2
(45) Date of Patent: May 12, 2020

(54) ORAL SUSTAINED-RELEASE TRIPLE LAYER TABLET

(75) Inventors: Jun Sang Park, Yongin-si (KR); U-Hun Song, Seongnam-si (KR); Ji-Yeon Sim, Seongnam-si (KR)

(73) Assignee: GL PHARMTECH CORP., Gyeonggi-Do (KR)

( * ) Notice: Subject to any disclaimer, the term of this patent is extended or adjusted under 35 U.S.C. 154(b) by 983 days.

(21) Appl. No.: 12/525,058

(22) PCT Filed: Feb. 11, 2008

(86) PCT No.: PCT/KR2008/000794
§ 371 (c)(1),
(2), (4) Date: Jul. 29, 2009

(87) PCT Pub. No.: WO2008/097066
PCT Pub. Date: Aug. 14, 2008

(65) Prior Publication Data
US 2010/0040681 A1     Feb. 18, 2010

(30) Foreign Application Priority Data
Feb. 7, 2007   (KR) ......................... 10-2007-0012944

(51) Int. Cl.
*A61K 9/28*     (2006.01)
*A61K 9/30*     (2006.01)
(Continued)

(52) U.S. Cl.
CPC ............ *A61K 9/209* (2013.01); *A61K 9/2086* (2013.01)

(58) Field of Classification Search
CPC ..... A61K 9/2086; A61K 9/209; A61K 9/2853; A61K 9/2866
See application file for complete search history.

(56) References Cited

U.S. PATENT DOCUMENTS 4,992,277 A * 2/1991 Sangekar et al. ............. 424/465
5,422,123 A * 6/1995 Conte et al. ................... 424/479
(Continued)

FOREIGN PATENT DOCUMENTS

EP     0432607 A1   6/1991
EP     0656204 A1   6/1995
(Continued)

OTHER PUBLICATIONS

Dow Chemical Company. Using Dow Excipients for Controlled Release of Drugs in Hydrophili Matrix Systems (2006), accessed at www.dow.com Jun. 25, 2011.*
(Continued)

*Primary Examiner* — Lakshmi S Channavajjala
(74) *Attorney, Agent, or Firm* — Harness, Dickey & Pierce, P.L.C.

(57) ABSTRACT

The present invention relates to an oral sustained-release triple layer tablet, more particularly, a triple layer tablet consisting of an inner immediate-release layer containing a pharmaceutically active ingredient and two outer layers containing swellable polymers. Upon exposure to aqueous media, the two outer layers swell to form gelled layers surrounding the lateral side of the inner layer rapidly, thereby control effectively the release of the pharmaceutically active ingredient from the inner immediate-release layer.

16 Claims, 2 Drawing Sheets

Initial              After 1 hour        After 3 hours

Cross-sectional view of dried tablet after 3 hours

(51) Int. Cl.
*A61K 9/24* (2006.01)
*A61K 9/20* (2006.01)

(56) References Cited

U.S. PATENT DOCUMENTS

| | | | | |
|---|---|---|---|---|
| 5,425,950 | A * | 6/1995 | Dandiker | A61K 9/209 |
| | | | | 424/474 |
| 5,549,913 | A * | 8/1996 | Colombo et al. | 424/472 |
| 5,626,874 | A * | 5/1997 | Conte | A61K 9/2086 |
| | | | | 424/464 |
| 5,783,212 | A * | 7/1998 | Fassihi | A61K 9/2086 |
| | | | | 424/464 |
| 6,003,685 | A | 12/1999 | Malin | 424/464 |
| 6,730,321 | B2 | 5/2004 | Ting et al. | |
| 2003/0180362 | A1* | 9/2003 | Park et al. | 424/470 |
| 2003/0203024 | A1* | 10/2003 | Sako et al. | 424/468 |
| 2005/0038007 | A1* | 2/2005 | Curatolo et al. | 514/171 |
| 2005/0100603 | A1* | 5/2005 | Sako et al. | 424/468 |
| 2006/0024368 | A1* | 2/2006 | Fassihi | A61K 9/0065 |
| | | | | 424/473 |
| 2006/0280795 | A1* | 12/2006 | Penhasi | A61K 9/4891 |
| | | | | 424/472 |

FOREIGN PATENT DOCUMENTS

| | | |
|---|---|---|
| EP | 1 095 650 | 5/2001 |
| EP | 1095650 A1 | 5/2001 |
| EP | 1382337 A1 | 1/2004 |
| JP | H072649 A | 1/1995 |
| JP | 2001-508440 | 6/2001 |
| JP | 2001-508440 A | 6/2001 |
| JP | 2005-162737 | 6/2005 |
| JP | 2005-162737 A | 6/2005 |
| WO | 9906035 A2 | 2/1999 |
| WO | 02098352 A2 | 12/2002 |

OTHER PUBLICATIONS

Maggi et al. International Journal of Pharmaceutics, 195: 229-238 (2000).*
Yang et al., Journal of Pharmacy and Pharmacology, 55: 1331-1337 (2003).*
Siahi et al. (AAPS PharmSciTech, 6 (4): E626-E632 (2005).*
Park et al., Drug Development and Industrial Pharmacy, 37(6): 664-672 (2011).*
Hodges et al., International Journal of Pharmaceutics, 454: 41-46 (2013).*
Conte et al., Biomaterials, 17: 889-896 (1996).*
Dow, "POLYOX Water-soluble Resins" (2004)) downloaded from http://msdssearch.dow.com/PublishedLiteratureDOWCOM/dh_0171/0901b80380171e3a.pdf?filepath=polyox/pdfs/noreg/326-00013.pdf%26fromPage=GetDoc on Sep. 19, 2016.*
International Search Report, dated Jun. 3, 2008, issued in corresponding International Application No. PCT/KR2008/000794, filed Feb. 11, 2008.

* cited by examiner

[Figure 1]
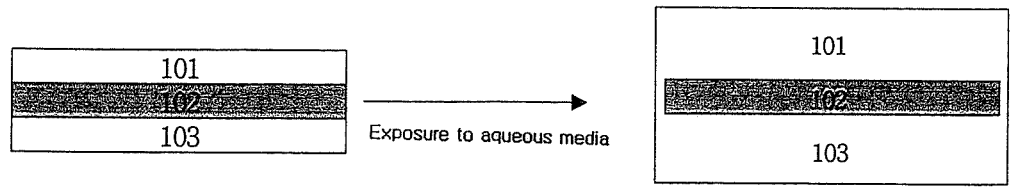
[Figure 2]
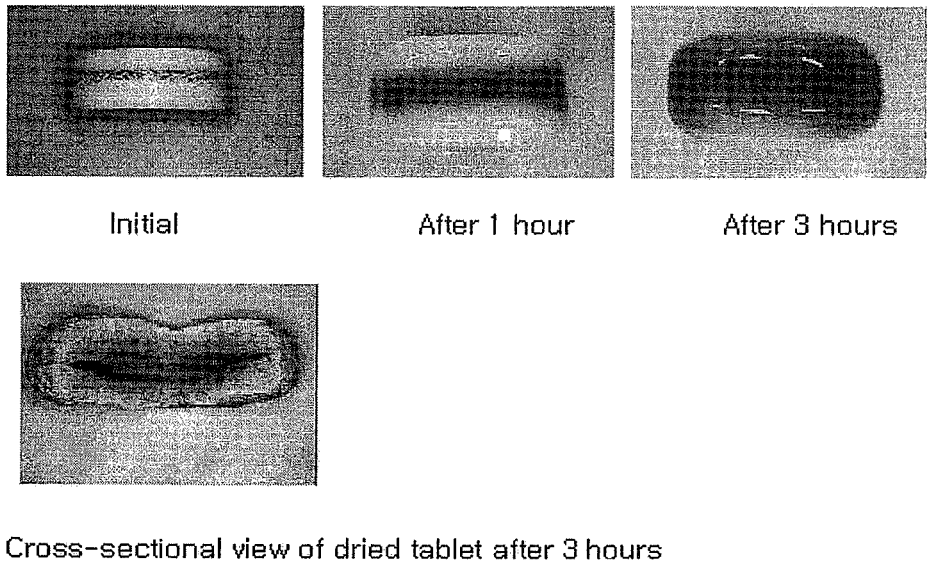
Cross-sectional view of dried tablet after 3 hours

[Figure 3]
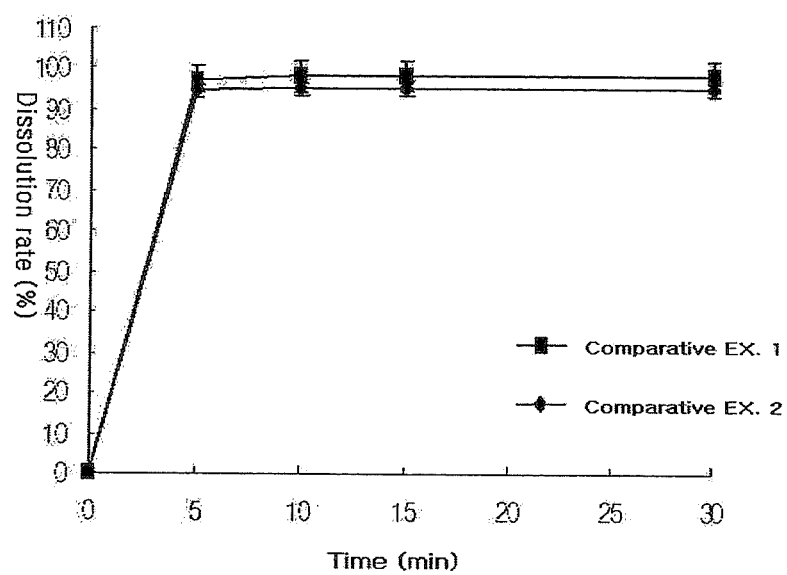
[Figure 4]
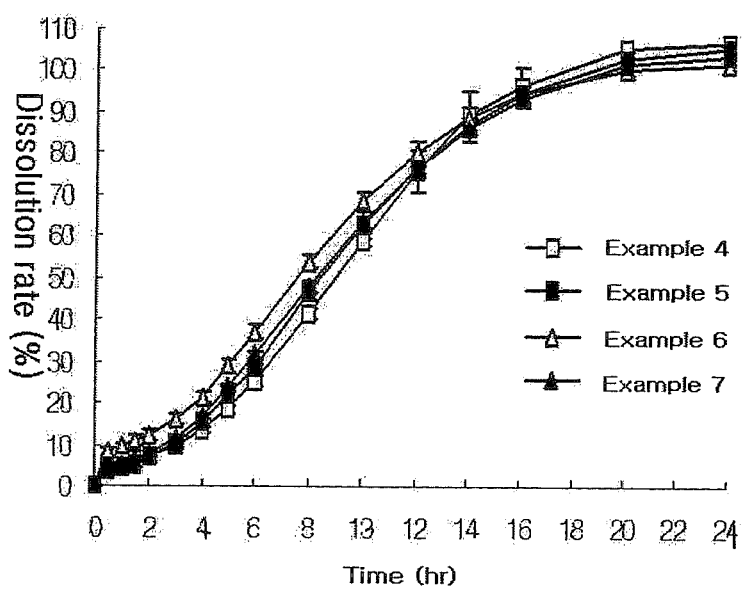

ORAL SUSTAINED-RELEASE TRIPLE LAYER TABLET

TECHNICAL FIELD

The present invention relates to an oral sustained-release triple layer tablet, more particularly, a triple layer tablet consisting of an inner immediate-release layer containing a pharmaceutically active ingredient and two outer layers containing swellable polymers. On exposure to aqueous media, the two outer layers swell to form gelled layers surrounding the lateral side of the inner layer rapidly, thereby control effectively the release of drug from the inner immediate-release layer.

BACKGROUND ART

Oral sustained-release formulation is developed to control the release of active ingredient at a designed rate and to obtain its optimal blood concentration therapeutically. This property leads to the reduction of the administration frequency, which helps to increase patient compliance and prevent adverse effects.

In order to achieve the object, a variety of dosage forms have been developed. Among them, because of simple composition and ease of manufacture, many studies have been conducted on a matrix system, in which active ingredients are dispersed in polymers which control the release rate However, the release from the simple matrix containing water-soluble polymers such as hydroxypropylmethylcellulose is subject to Fickian diffusion, which causes some drawbacks such as an initial burst.

There have been attempts to introduce an additional release-controlling layer into the matrix formulation, for the purpose of avoiding an initial burst and initiating the release of active ingredient after a predetermined time.

U.S. Pat. No. 5,422,123 discloses a tablet consisting of a core and a support applied to the core to partly cover its surface, in which the release of pharmaceutically active ingredient is controlled as follows: The core contains the drug and a polymer which swells and gelates upon contact with aqueous media in a ratio of 1:9 to 9:1, based on the amount of drug, so that the release of pharmaceutically active ingredient is controlled by the same mechanism as in the matrix formulation, but the support containing a polymer which is slowly soluble or gellable in aqueous media controls the surface area of the core and varies the release patterns.

U.S. Pat. No. 5,549,913 discloses a multilayer tablet for release of pharmaceutically active ingredient at a constant rate with a zero order kinetic profile, in which two outer layers contain pharmaceutically active ingredient and hydrophilic polymers, and an inner layer contains a water-soluble polymer without the pharmaceutically active ingredient. The inner layer is readily dissolved in aqueous media to separate the two outer layers, and thus to increase the surface area of the matrix.

U.S. Pat. No. 5,626,874 discloses a multilayer tablet consisting of two outer layers containing gellable or erodible polymers and an inner layer containing an active ingredient. The side surface of the inner layer occupies about 5 to 35% of the tablet's total surface.

U.S. Pat. No. 5,783,212 discloses a multilayer tablet for release of pharmaceutically active ingredient at a constant rate with a zero order kinetic profile, in which two outer layers contain swellable and erodible polymers, an inner layer contains a pharmaceutically active ingredient and swellable and erodible polymers, and each layer differs in composition and thickness.

U.S. Pat. No. 6,730,321 discloses a press-coated tablet that facilitates a pulsatile release of pharmaceutically active ingredient, consisting of an immediate-release core and a sustained-release layer, which is press-coated.

In the above prior arts, an immediate-release inner layer containing pharmaceutically active ingredient is not introduced or, even if introduced, the immediate-release inner layer is completely coated with the controlling layers. This is because if the inner layer of the triple layer tablet does not contain polymers to control the release and is exposed to aqueous media, there will be several problems; namely, excessive initial burst, layer separation due to loss of the inner immediate-release layer, and significant deviation in release rate, which can be fully predicted by those skilled in the art.

The present inventors have found that surprisingly although an inner immediate-release layer containing a pharmaceutically active ingredient is not completely coated but contacted with two outer layers, if said layers contain swellable polymers, those two outer layers swell to form gelled layers surrounding the lateral side of the inner layer rapidly upon exposure to aqueous media acting to control the release of active ingredient from the inner immediate-release layer uniformly and reproducibly, thereby completing the present invention.

DISCLOSURE

Technical Problem

The object of the present invention is to provide a sustained-release triple layer tablet, consisting of an inner immediate-release layer containing a pharmaceutically active ingredient and two outer layers containing swellable polymers. On exposure to aqueous media, the two outer layers swell to form gelled layers surrounding the lateral side of the inner layer, thereby controlling effectively the release of drug from the inner immediate-release layer.

Technical Solution

In order to achieve the object, the present invention provides a sustained-release triple layer tablet, consisting of an inner layer which releases drug immediately by itself and two outer layers which contain swellable polymers controlling the release of drug from the triple-layer tablet.

Advantageous Effects

When the oral sustained-release triple layer tablet according to the present invention is exposed to aqueous media, the two outer layers swell to form gelled layers surrounding the lateral side of the inner layer, thereby effectively controlling the release of pharmaceutically active ingredient from the inner immediate-release layer. The above triple layer tablet can reduce an initial burst, one of the drawbacks of the matrix, and achieve a variety of release patterns allowing for several kinds of sustained-release tablets.

DESCRIPTION OF DRAWINGS

FIG. 1 shows an oral sustained-release triple layer tablet, consisting of an inner immediate-release layer (102) containing a pharmaceutically active ingredient, an upper outer layer (101) and lower outer layer (103) containing swellable polymers;

FIG. 2 shows the results of the stirring and gelling test of Example 1;

FIG. 3 shows the results of the dissolution test of Comparative Examples 1 and 2; and FIG. 4 shows the results of the dissolution test of Examples 3 to 6.

BEST MODE

The triple layer tablet of the present invention is characterized in that upon exposure to aqueous media, the two outer layers swell to form gelled layers surrounding an inner immediate-release layer, thereby controlling the release of pharmaceutically active ingredient from the inner layer.

Hereinafter, the sustained-release triple layer tablet according to the present invention will be described in more detail.

In the present invention, the inner immediate-release layer is contained in an amount of 5 to 60 w/w %, preferably 10 to 40 w/w %, based on the total weight of the tablet.

Examples of the pharmaceutically active ingredient contained in the inner immediate-release layer may include antihypertensives (doxazosin mesylate, terazosin hydrochloride, etc.), anti-benign prostatic hyperplasia agents (tamsulosin hydrochloride, etc.), antihyperlipidemics (simvastatin, lovastatin, fluvastatin, etc.), nonsteroidal anti-inflammatory drugs (acetaminophen, zaltoprofen, etc.), analgesic drugs (tramadol hydrochloride, etc.), antidiabetes drugs, and hypnotics.

It is preferable that, when the dissolution test is performed in aqueous media, 80% or more of the pharmaceutically active ingredient is released from the inner immediate-release layer without the outer layers within 1 hour.

In addition to the pharmaceutically active ingredient, the inner immediate-release layer may further include pharmaceutically acceptable excipients (e.g., lactose, dextrose, sucrose, dextrate, mannitol, sorbitol, xylitol, sodium chloride, magnesium chloride, calcium phosphate dibasic, citric acid, microcrystalline cellulose, etc.), binders (e.g., copovidone, polyvinylpyrrolidone, hydroxypropylcellulose, etc.), disintegrants (e.g., sodium starch glycolate, croscarmellose sodium, crospovidone, low-substituted hydroxypropylcellulose), lubricants (e.g., magnesium stearate, stearic acid, sodium stearyl fumarate, colloidal silicone dioxide, etc.), or the like.

In the present invention, the dissolution media quickly permeates the sustained-release triple layer tablet through the inner immediate-release layer, and is rapidly supplied to the swellable polymers of the two outer layers in contact with the inner layer to facilitate the formation of gelled layers surrounding the inner layer.

In the present invention, the two outer layers contain the swellable polymer in an amount of 40 to 95 w/w %, preferably 60 to 90 w/w %, based on the total weight of the tablet. The compositions and amounts of the two outer layers may be the same or different from each other, as required.

The polymers contained in the two outer layers are swellable upon exposure to aqueous media, and examples thereof may include polyethyleneoxide, hydroxypropylmethylcellulose, hydroxypropylcellulose, carboxymethylcellulose, polyvinylalcohol, carbomer and so on, preferably polyethyleneoxide having a viscosity of 400 cps or more (in 2% aqueous solution) and hydroxypropylmethylcellulose having a viscosity of 4000 cps or more (in 2% aqueous solution).

For the purpose of obtaining various dissolution profiles, the two outer layers may optionally include a pharmaceutically active ingredient. In an embodiment, the pharmaceutical active ingredient in an outer layer may be the pharmaceutically active ingredient contained in the inner immediate-release layer.

The two outer layers may additionally include pharmaceutically acceptable excipients (e.g., lactose, dextrose, sucrose, dextrate, mannitol, sorbitol, xylitol, sodium chloride, magnesium chloride, calcium phosphate dibasic, citric acid, microcrystalline cellulose), binders (e.g., copovidone, polyvinylpyrrolidone, hydroxypropylcellulose), lubricants (e.g., magnesium stearate, stearic acid, sodium stearyl fumarate, colloidal silicone dioxide), or the like.

In the present invention, when the sustained-release triple layer tablet is exposed to aqueous media, the two outer layers swell to form gelled layers surrounding the inner immediate-release layer. This effect can prevent an initial burst of pharmaceutically active ingredient from the inner immediate-release layer and ensures that the tablet strength is not separated into each layer by gastrointestinal motility. Further, the gelled layer becomes a release-controlling membrane, making the sustained release dosage form.

In addition, the present invention provides a method for preparing the oral sustained-release triple layer tablet, comprising the steps of:

mixing the drug and pharmaceutically acceptable additives and optional granulating to prepare mixtures for the inner immediate-release layer of sustained-triple layer tablets;

mixing the swellable polymers, pharmaceutically acceptable additives, and optional drug and optionally granulating to prepare each mixture for the two outer layers; and tabletting the mixtures in turn.

The above tablets are prepared by a conventional method. That is, ingredients of each layer are mixed using a mixer, and then directly compressed using a multilayer tabletting machine, or ingredients of each layer are mixed to prepare granules using a machine such as a vertical granulator and a roller compactor, and then compressed to prepare the oral sustained-release triple layer tablet.

MODE FOR INVENTION

Hereinafter, the present invention will be described in more detail with examples. However, these examples are for the illustrative purpose only, and the invention is not intended to be limited by these examples.

Examples 1 and 2

According to table 1, aqueous pigment (Yellow No. 5), copovidone, and dextrate passed through a 50 mesh sieve were blended for an inner layer, and a swellable polymer such as polyethyleneoxide (commercial name: Polyox WSR Coagulant, Dow Chemicals) or hydroxypropylmethylcellulose (commercial name: Methocel 100M CR, Dow Chemicals) and magnesium stearate passed through a 30 mesh sieve were blended for two outer layers. Each mixture was compressed in turn to be a triple layer tablet with a diameter of 9.0 mm at the final pressure of 6 MPas using a hydraulic press.

TABLE 1

Compositions of Examples 1 and 2 (unit: mg)

| Layers | Ingredients | Example 1 | Example 2 |
|---|---|---|---|
| Upper layer | Polyethyleneoxide (Polyox WSR Coagulant ™) | 99.5 | — |
| | Hydroxypropylmethylcellulose (Methocel K100M CR ™) | — | 99.5 |
| | Magnesium stearate | 0.5 | 0.5 |
| Intermediate layer | Yellow No. 5 | 1.0 | 1.0 |
| | Dextrate | 46.5 | 46.5 |
| | Copovidone | 2.5 | 2.5 |
| Lower layer | Polyethylene oxide (Polyox WSR Coagulant ™) | 99.5 | — |
| | Hydroxypropyl methylcellulose (Methocel K100M CR ™) | — | 99.5 |
| | Magnesium stearate | 0.5 | 0.5 |
| | Total | 250.0 | 250.0 |

Examples 3 to 6

According to table 2, terazosin hydrochloride dihydrate, copovidone, and dextrate or lactose passed through a 50 mesh sieve were blended for an inner layer, and polyethyleneoxide (commercial name: Polyox WSR Coagulant, Dow Chemicals) and magnesium stearate passed through a 30 mesh sieve were blended for two outer layers. Each mixture was compressed in turn to be a triple layer tablet with a diameter of 9.0 mm at the final pressure of 6 MPas using a hydraulic press.

TABLE 2

Compositions of Examples 3 to 6 (unit: mg)

| Layers | Ingredients | Example 3 | Example 4 | Example 5 | Example 6 |
|---|---|---|---|---|---|
| Upper layer | Polyethyleneoxide (Polyox WSR Coagulant ™) | 99.500 | 99.500 | 99.500 | 99.500 |
| | Magnesium stearate | 0.500 | 0.500 | 0.500 | 0.500 |
| Intermediate layer | Terazosin hydrochloride dihydrate | 3.561 | 3.561 | 3.561 | 3.561 |
| | Lactose | 62.939 | 24.939 | — | — |
| | Dextrate | — | — | 62.939 | 24.939 |
| | Copovidone | 3.500 | 1.500 | 3.500 | 1.500 |
| Lower layer | Polyethyleneoxide (Polyox WSR Coagulant ™) | 99.500 | 99.500 | 99.500 | 99.500 |
| | Magnesium stearate | 0.500 | 0.500 | 0.500 | 0.500 |
| | Total | 270.00 | 230.00 | 270.00 | 230.00 |

Examples 7 and 8

According to table 3, a solution of tamsulosin hydrochloride and povidone K30 dissolved in 4 mg of purified water per tablet was added to lactose, kneaded, dried and granulated. Then, copovidone and dextrate passed through a 50 mesh sieve were blended for an inner layer, and polyethyleneoxide (commercial name: Polyox WSR Coagulant, Dow Chemicals) and magnesium stearate passed through a 30 mesh sieve were blended for two outer layers. Each mixture was compressed in turn to be a triple layer tablet with a diameter of 9.0 mm at the final pressure of 6 MPas using a hydraulic press.

TABLE 3

Compositions of Examples 7 and 8 (unit: mg)

| Layers | Ingredients | Example 7 | Example 8 |
|---|---|---|---|
| Upper layer | Polyethyleneoxide (Polyox WSR Coagulant ™) | 99.50 | 99.50 |
| | Magnesium stearate | 0.50 | 0.50 |
| Intermediate layer | Tamsulosin hydrochloride | 0.40 | 0.40 |
| | Povidone K30 | 1.80 | 1.80 |
| | Lactose | 53.60 | 53.60 |
| | Copovidone | 4.20 | 7.00 |
| | Dextrate | — | 37.20 |
| Lower layer | Polyethyleneoxide (Polyox WSR Coagulant ™) | 99.50 | 99.50 |
| | Magnesium stearate | 0.50 | 0.50 |
| | Total | 260.00 | 300.00 |

Comparative Examples 1 and 2

According to table 4, terazosin hydrochloride dihydrate, copovidone, and dextrate or lactose passed through a 50 mesh sieve were blended to prepare a tabletting composition. The mixture was compressed into a tablet with a diameter of 9.0 mm, at the pressure of 6 MPas using a hydraulic press.

TABLE 4

Compositions of Comparative Examples 1 and 2 (unit: mg)

| Ingredients | Comparative Example 1 | Comparative Example 2 |
|---|---|---|
| Terazosin hydrochloride dihydrate | 3.561 | 3.561 |
| Lactose | 62.939 | — |
| Dextrate | — | 62.939 |
| Copovidone | 3.500 | 3.500 |
| Total | 70.000 | 70.000 |

Comparative Example 3

According to table 5, a solution of tamsulosin hydrochloride and povidone K30 dissolved in 4 mg of purified water per tablet was added to lactose, kneaded, dried and granulated. After being mixed with copovidone, the mixture was compressed into a tablet with a diameter of 9.0 mm at the pressure of 6 MPas using a hydraulic press

TABLE 5

Composition of Comparative Example 3 (Unit: mg)

| Ingredients | Comparative Example 3 |
|---|---|
| Tamsulosin hydrochloride | 0.40 |
| Povidone K30 | 1.80 |
| Lactose | 53.60 |
| Copovidone | 4.20 |
| Total | 60.00 |

Test 1: Stirring and gelling test

A stirring and gelling test for Example 1 was performed to confirm whether, upon exposure to aqueous media, the triple layer tablet formed gelled layers surrounding the inner layer and whether the layers separated or not. Stirring was performed in 900 mL of pH 6.8 phosphate buffer (Korean Pharmacopoeia, disintegration test $2^{nd}$ solution) using a magnetic stirrer. The results are shown in FIG. 2.

FIG. 2 shows that the triple layer tablet of Example 1 formed gelled layers, upon exposure to aqueous media, surrounding the inner layer as the two outer layers swell. Further, that no layer separation occurred after stirring for 3 hours provided that the triple layer tablet was strong enough to endure gastrointestinal motility and to control the release of drug from the inner layer. The swollen triple layer tablet after 3 hours of testing was completely dried in a drier. As shown in the cross-sectional view, the inner immediate-release layer at initial exposure was surrounded by the two swollen outer layers, and completely isolated from the dissolution media by a gelled layer.

Test 2: Dissolution test

Dissolution tests for Comparative Examples 1 and 2 and Examples 4 to 7 were performed in 900 mL of pH 6.8 phosphate buffer (Korean Pharmacopoeia, disintegration test 2 solution) at 100 rpm using the paddle method. The results are shown in FIGS. 3 and 4.

Comparative Examples 1 and 2 show tablets composed of the inner immediate-release layer of a triple layer tablet only wherein 90% or more of active ingredients were released within 30 min. In contrast, it was found that since the triple layer tablets of Examples 4 to 7 had outer layers containing a swellable polymer to control the release on the upper and lower sides of the inner immediate-release layer, the two outer layers surrounded the lateral side of the inner immediate-release layer to effectively control the release of pharmaceutically active ingredient from the inner layer for about 24 hrs.

The present invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. An oral sustained-release triple-layer tablet comprising:
    an inner immediate-release layer comprising a pharmaceutically active ingredient and a binder, and
    two outer layers, each outer layer comprising a swellable polymer which is polyethylene oxide having a viscosity of 400 cps or greater in 2% aqueous solution, or hydroxypropyl methylcellulose having a viscosity of 4,000 cps or greater in 2% aqueous solution, or a mixture of the polyethylene oxide and the hydroxypropyl methylcellulose,
    wherein the inner immediate-release layer has an exposed lateral side which is not covered by the two outer layers,
    wherein only the two outer layers comprise the swellable polymer, and the two outer layers swell upon exposure to aqueous medium to form gelled layers that surround the exposed lateral side of the inner immediate-release layer, and
    wherein the two outer layers comprise 40 to 95% by weight of the swellable polymer, based on the total weight of the tablet.

2. The oral sustained-release triple layer tablet of claim 1, wherein the inner immediate-release layer is characterized during dissolution testing in an aqueous medium such that 80% or more of the pharmaceutically active ingredient released from the inner immediate-release layer without the outer layers within one hour from exposure to the aqueous medium.

3. The oral sustained-release triple layer tablet of claim 1, wherein the inner immediate-release layer further comprises a pharmaceutically acceptable excipient.

4. The oral sustained-release triple layer tablet of claim 1, wherein the pharmaceutically active ingredient is selected from the group consisting of doxazosin, terazosin, tamsulosin, simvastatin, lovastatin, fluvastatin, acetaminophen, zaltoprofen and tramadol.

5. The oral sustained-release triple layer tablet of claim 3, wherein the pharmaceutically active ingredient is terazosin or tamsulosin.

6. The oral sustained-release triple layer tablet of claim 1, wherein the two outer layers containing the swellable polymer include a pharmaceutically acceptable excipient, binder, disintegrant or lubricant.

7. The oral sustained-release triple layer tablet of claim 1, wherein each of the two outer layers containing the swellable polymer include a pharmaceutically active ingredient.

8. The oral sustained-release triple layer tablet of claim 1, wherein the inner immediate-release layer is included in an amount of 5 to 60% by weight, based on the total weight of the tablet.

9. The oral sustained-release triple layer tablet of claim 8, wherein the two outer layers comprise 60 to 90% by weight of the swellable polymer, based on the total weight of the tablet.

10. An oral sustained-release triple-layer tablet comprising:
    an inner immediate-release layer comprising a pharmaceutically active ingredient and a binder, wherein the pharmaceutical active ingredient is selected from the group consisting of doxazosin, terazosin, tamsulosin, simvastatin, lovastatin, fluvastatin, acetaminophen, zaltoprofen and tramadol, and
    two outer layers comprising polyethylene oxide having a viscosity of 400 cps or greater in 2% aqueous solution,
    wherein the inner immediate-release layer is characterized during dissolution testing in an aqueous medium such that 80% or more of the pharmaceutically active ingredient is released from the inner immediate-release layer without the outer layers within one hour from exposure to the aqueous medium,
    wherein the inner immediate-release layer has an exposed lateral side which is not covered by the two outer layers, wherein only the two outer layers comprise the polyethylene oxide, and the two outer layers swell upon exposure to aqueous medium to form gelled layers that surround the exposed lateral side of the inner immediate-release layer, and
    wherein the oral sustained-release triple-layer tablet comprises 5 to 60% by weight of the inner immediate-release layer and 40 to 95% by weight of the polyethylene oxide, based on the total weight of the tablet.

11. The oral sustained-release triple layer tablet of claim 1, wherein the swellable polymer of at least one of the two outer layers comprises the polyethylene oxide.

12. The oral sustained-release triple-layer tablet of claim 10, wherein the inner immediate-release layer further comprises a pharmaceutical acceptable excipient.

13. An oral sustained-release triple-layer tablet comprising:
    an inner immediate-release layer comprising a pharmaceutically active ingredient and a binder, wherein the pharmaceutical active ingredient is selected from the group consisting of doxazosin, terazosin, tamsulosin, simvastatin, lovastatin, fluvastatin, acetaminophen, zaltoprofen and tramadol, and two outer layers comprising polyethylene oxide having a viscosity of 400 cps or greater in 2% aqueous solution, wherein the inner immediate-release layer is characterized during dissolution testing in an aqueous medium such that 80% or more of the pharmaceutically active ingredient is released from the inner immediate-release layer without the outer layers within one hour from exposure to the aqueous medium, wherein the inner immediate-release layer has an exposed lateral side which is not covered by the two outer layers, wherein the two outer layers swell upon exposure to aqueous medium to form gelled layers that surround the exposed lateral side of the inner immediate-release layer, and wherein the oral sustained-release triple-layer tablet comprises 5 to 60% by weight of the inner immediate-release layer and 40 to 95% by weight of the polyethylene oxide, based on the total weight of the tablet.

14. The oral sustained-release triple-layer tablet of claim 13, wherein the inner immediate-release layer further comprises a pharmaceutical acceptable excipient.

15. An oral sustained-release triple-layer tablet comprising:

an inner immediate-release layer comprising a pharmaceutically active ingredient, a pharmaceutical acceptable diluent and a binder, and two outer layers, each outer layer comprising a swellable polymer which is polyethylene oxide having a viscosity of 400 cps or greater in 2% aqueous solution, or hydroxypropyl methylcellulose having a viscosity of 4,000 cps or greater in 2% aqueous solution, or a mixture of the polyethylene oxide and the hydroxypropyl methylcellulose, wherein the inner immediate-release layer is characterized during dissolution testing in an aqueous medium such that 80% or more of the pharmaceutically active ingredient is released from the inner immediate-release layer without the outer layers within one hour from exposure to the aqueous medium, wherein the inner immediate-release layer has an exposed lateral side which is not covered by the two outer layers, wherein the two outer layers swell upon exposure to aqueous medium to form gelled layers that surround the exposed lateral side of the inner immediate-release layer, and wherein the two outer layers comprise 40 to 95% by weight of the swellable polymer, based on the total weight of the tablet.

16. The oral sustained-release triple-layer tablet of claim 15, wherein the inner immediate-release layer further comprises a pharmaceutical acceptable excipient.

* * * * *